United States Patent
Foerster et al.

(10) Patent No.: US 6,303,109 B1
(45) Date of Patent: Oct. 16, 2001

(54) BODY CLEANSING AGENT

(75) Inventors: Thomas Foerster, Erkrath; Martina Hollenbrock, Duesseldorf; Wolfhard Scholz, Krefeld; Wolfgang Pittermann, Duesseldorf; Michael Schmitt, Haan, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/380,881

(22) PCT Filed: Mar. 3, 1998

(86) PCT No.: PCT/EP98/01174

§ 371 Date: Oct. 12, 1999

§ 102(e) Date: Oct. 12, 1999

(87) PCT Pub. No.: WO98/40044

PCT Pub. Date: Sep. 17, 1998

(30) Foreign Application Priority Data

Mar. 12, 1997 (DE) .............................. 197 10 149

(51) Int. Cl.$^7$ .................................. A61K 7/075
(52) U.S. Cl. ................ 424/70.31; 424/70.1; 424/70.19; 424/70.21; 424/70.22; 424/70.24; 424/70.9; 424/401
(58) Field of Search ........................ 424/59, 70.1, 70.19, 424/70.21, 70.22, 70.24, 70.31, 70.9, 401, 450, 489, 490, 498

(56) References Cited

U.S. PATENT DOCUMENTS

| | | | | |
|---|---|---|---|---|
| 4,454,159 | * | 6/1984 | Musher | 424/358 |
| 4,481,186 | * | 11/1984 | Deckner | 424/59 |
| 4,707,293 | * | 11/1987 | Ferro | 252/174.17 |
| 4,847,072 | * | 7/1989 | Bissett et al. | 424/59 |
| 5,098,606 | * | 3/1992 | Nakajima et al. | 252/358 |
| 5,658,575 | | 8/1997 | Ribier et al. | 424/401 |

FOREIGN PATENT DOCUMENTS

| | | |
|---|---|---|
| 43 18 171 | 12/1994 | (DE) . |
| 44 41 029 | 5/1996 | (DE) . |
| 0 641 557 | 3/1995 | (EP) . |
| 0 705 593 | 4/1996 | (EP) . |
| 2 666 015 | 2/1992 | (FR) . |

* cited by examiner

Primary Examiner—Thurman K. Page
Assistant Examiner—P. E. McQueeney
(74) Attorney, Agent, or Firm—Wayne C. Jaeschke; Glenn E. J. Murphy; Kimberly R. Hild

(57) ABSTRACT

The invention relates to lipid soluble, water insoluble cosmetic or dermatological active substances which can be included in body cleansing agents in the form of an aqueous preparation with at least 5 wt. % water soluble ionic or non-ionic surfactant content by solubilization of the active substances with a polar lipid in lipid-surfactant mixed micelles or liquid crystals or by microemulsification with a nonpolar lipid, wherein the emulsion particles have a diameter which is less than 500 nm. Said agents are also characterized by enhanced skin penetration by the active substances.

15 Claims, No Drawings

BODY CLEANSING AGENT

This application is filed under 35 U.S.C. 371 and based on PCT/EP98/01174, filed Mar. 3, 1998,

BACKGROUND OF THE INVENTION

1. Field of the Invention

This invention relates to body washes based on aqueous preparations of water-soluble surfactants in which lipid-soluble cosmetic or pharmaceutical active substances are incorporated in a manner which ensures increased absorption of the active substances into the skin during the washing process.

2. Discussion of Related Art

It is known that cosmetic or dermatological agents can be added to body washes in order to exert a dermatologically favorable or cosmetically desirable influence on the condition of the skin during the washing process.

Hitherto, however, only water-soluble active substances have been suitable for this purpose because it is only water-soluble active substances which come into contact with the skin sufficiently to develop an effect in the relatively short time taken by the washing process. Although attempts have been made to incorporate oil-soluble active substances in water-based body washes by emulsification or solubilization, the resulting effects on the skin were not satisfactory because the active substances were either encapsulated in emulsion droplets or solubilized in surfactant micelles.

Accordingly, attempts have been made to find ways of incorporating lipid-soluble active substances in a homogeneous and stable manner in water-based body washes and, at the same time, to achieve improved penetration of the active substances during the relatively short contact time with the skin. As a result of these various attempts, it was found that improved skin penetration can be achieved if the active substances in question are present as a component in lipid/surfactant mixed micelles, lipid microemulsions or wax nanoparticles with an average particle size below 500 nm.

DESCRIPTION OF THE INVENTION

Accordingly, the present invention relates to body washes in the form of an aqueous preparation containing at least 5% by weight of water-soluble surfactants and at least 0.05% by weight of a lipid-soluble cosmetic or dermatological active substance which is solubilized with a polar lipid in lipid/surfactant mixed micelles or liquid crystals or is microemulsified with a non-polar lipid the emulsion droplets essentially having a diameter of less than 500 nm.

Body washes in the context of the present invention are liquid or paste-form aqueous preparations such as, for example, liquid soaps, wash lotions, shower bath preparations, foam baths or hair shampoos which are applied to clean the skin or the scalp and hair and which are rinsed off with water. Water-soluble surfactants in the context of the invention are ionic or nonionic surfactants of which at least 5% by weight dissolves clearly in water at 20° C. Particularly suitable water-soluble surfactants are, for example, high-foaming anionic sulfate or sulfonate surfactants, ampholytic, zwitterionic, nonionic surfactants or mixtures thereof. Examples of such high-foaming anionic surfactants are $C_{12-16}$ alkyl sulfates, for example in the form of their alkanolamine salts, $C_{12-16}$ alkyl polyglycol ether sulfates, acyl isethionates, acyl sarcosides, fatty acid monoglyceride sulfates, for example in the form of their alkali metal, ammonium or magnesium salts.

Suitable zwitterionic surfactants are, above all, betaine surfactants, for example $C_{12-18}$ alkyl dimethyl acetobetaine, cocoacylamidopropyl dimethylacetobetaine or imidazolinium betaines and sulfobetaines.

Suitable high-foaming surfactants are, above all, mixtures of the above-mentioned anionic sulfate and sulfonate surfactants and zwitterionic betaine surfactants. Mixtures of anionic surfactants and nonionic alkyl glycoside surfactants are also known to foam particularly vigorously.

Suitable nonionic surfactants besides the alkyl glycosides and alkyl (oligo)glucosides mentioned above are methyl glucoside fatty acid esters and ethylene oxide adducts thereof. Other suitable nonionic surfactants are, finally, products of the addition of ethylene oxide onto fatty alcohols, fatty acids, fatty acid monoglycerides, sorbitan fatty acid esters, alkyl glucosides, fatty acid alkanolamides and other fatty compounds containing hydroxyl or carboxyl groups, providing they are sufficiently soluble in water. This is generally the case if the content of lipophilic acyl or alkyl groups in the molecule makes up less than 50% by weight.

The body washes according to the invention contain the water-soluble surfactants in a quantity of preferably 5 to 30% by weight and more preferably 0.1 to 1% by weight of a lipid-soluble vitamin as active substance.

Lipid-soluble cosmetic or pharmaceutical active substances in the context of the invention are, above all, dermatologically active compounds which, for example, have an inflammation-inhibiting, local anaesthetic, skin-softening, antimicrobial, radiation-absorbing, skin-protecting, circulation-promoting or anti-skin-ageing effect and which are barely soluble in water, but soluble in paraffin oil, for example, in a quantity of more than 1% by weight.

Particularly suitable lipid-soluble active substances are, for example, vitamins, such as vitamin A (retinols), vitamin E (tocopherols), vitamin F (polyene fatty acids), β-carotene (provitamin A), and lipid-soluble derivatives (for example esters) thereof. Lipid-soluble esters of ascorbic acid, for example stearyl ascorbate, are also suitable. However, natural or synthetic tocopherols and lipid-soluble derivatives thereof are preferably used in the body washes according to the invention.

Suitable tocopherols are, for example, natural tocopherols and mixtures thereof and also synthetic tocopherols. Suitable esters are, for example, tocopherol acetate, tocopherol nictinate, tocopherol ascorbate, tocopheryl retinoate, tocopheryl succinate, tocopheryl linoleate and tocopheryl benzoate.

Polar lipids in the context of the invention are fatty compounds containing one or two linear $C_{12-22}$ alkyl or acyl groups and a hydrophilic group of which the size is not sufficient to make the molecule soluble in water. Hydrophilic groups such as these are, for example, the hydroxyl group, a dihydroxyethyl group or a polyhydroxyalkoxy group containing 3 to 6 carbon atoms and 2 to 5 hydroxyl groups. Polar lipids of the type in question are often referred to as "lipophilic co-emulsifiers". Suitable examples of such lipids are, for example, cetyl and stearyl alcohol, 1,2-dodecanediol, glycerol monocetyl ether, glycerol monostearate, stearyl monoglucoside, sorbitan monopalmitate or methyl glucoside dioleate.

Other lipids are the phospholipids (lecithins) and the sterols (for example cholesterol and vegetable sterols).

Lipid/surfactant mixed micelles or lamellar liquid crystals containing lipid-soluble active substances are obtained when mixtures of the active substance, a polar lipid and a water-soluble surfactant as dispersant are heated with water to a temperature above the melting point of the lipid and mixed. The ratio by weight of lipid to dispersant is adjusted so that a lamellar liquid crystal dispersion or—below the melting temperature—a lamellar gel phase, which can form lipid/surfactant mixed micelles on dilution with water, is formed. The viscosity of this gel phase can be reduced to the flowable range by addition of short-chain $C_{1-4}$ alcohols or glycols, for example ethanol or propylene glycol. The ratio by weight of lipid to dispersant is preferably 1:2 to 2:1. The ratio by weight of polar lipid to lipid-soluble active substance is preferably 10:0.2 to 10:2.

The body washes according to the invention are preferably produced by preparing a concentrate of the active substance solubilized in lipid/surfactant mixed micelles or liquid crystals with a content of 1 to 10% by weight of the active substance and mixing the resulting concentrate with the aqueous body wash. Depending on the quantity ratio between the lamellar liquid crystal concentrate added and the aqueous surfactant preparation of the body wash, the resulting product may be a transparent, optically isotropic product (mixed micelles) or a cloudy product containing lamellar emulsion droplets which should be no larger than 500 nm in size. Accordingly, a transparent product which contains the lipid/vitamin complex in the form of mixed micelles should preferably be obtained.

Non-polar lipids in the context of the invention are paraffins, fatty acid ($C_{12-22}$) triglycerides, waxes and cosmetic oil and fatty components, such as full esters of fatty acids with monohydric and polyhydric alcohols or full esters of fatty alcohols with monobasic and polybasic carboxylic acids. Particularly suitable non-polar lipids are paraffins, triglycerides and waxes solid at 20° C., such as for example hard paraffin, hydrogenated castor oil, cetyl palmitate and other wax esters solid at 200° C.

Microemulsions in the context of the present invention are fine-droplet emulsions with a droplet size below 500 nm and preferably below 300 nm. They may be prepared in known manner, for example in accordance with DE 44 41 029 A1 or DE 43 18 171 A1. In these known processes, the lipid-soluble active substances are heated with the non-polar lipid and the dispersant in water to a temperature above the phase inversion temperature, emulsified and cooled while stirring to normal temperature (20° C.). Shimmering blue, very fine-droplet dispersions are obtained. Where waxes are used as the non-polar lipids, they are present in the form of nanoparticles with a particle size (diameter) below 500 nm and preferably between 100 and 200 nm.

The active substances are preferably converted with the non-polar lipids, for example with waxes, into a concentrated microemulsion containing 1 to 10% by weight of the active substances and then mixed with the aqueous body wash. The particle size of the lipid microemulsions or the wax nanoparticles generally remains unchanged during this step.

The present invention also relates to the use of aqueous preparations containing at least 5% by weight of water-soluble surfactants and at least 0.05% by weight of a lipid-soluble, water-insoluble, cosmetic or dermatological active substance which is solubilized with a polar lipid in lipid/surfactant mixed micelles or microemulsified with a non-polar lipid, the emulsion droplets having a diameter of less than 500 nm, for washing and cleaning the skin and the hair and for increasing the absorption of the active substance into the skin.

The body washes according to the invention are suitable for achieving a cosmetic or dermatological effect on the skin simply by application during showering, bathing or washing of the hands. For uses such as these, it is particularly preferred for the body wash to contain a linear $C_{12-22}$ fatty alcohol, a linear $C_{12-22}$ alkanediol, a $C_{12-22}$ fatty acid partial ester of a $C_{3-8}$ polyol containing 2 to 6 hydroxyl groups or a $C_{8-22}$ fatty acid mono-alkanolamide as the polar lipid and optionally a paraffin solid at 20° C., a fatty acid ($C_{12-22}$) triglyceride, a wax ester or a mixture thereof as the non-polar lipid and for the polar and non-polar lipids to be present in a quantity of 5 to 50 parts by weight, based on 1 part by weight of the active substance.

The following Examples are intended to illustrate the invention.

EXAMPLES

1. Preparation of the active substance concentrates 1.1 Solubilization in lipid/surfactant or liquid crystal dispersion

|  | S1 | S2 | S3 |
|---|---|---|---|
| Vitamin E acetate | 1.8 | 2.1 | 2.9 |
| Vitamin F (linoleic acid) | 3.6 | 3.4 | 4.8 |
| Glycerol monooleate | 23.0 | 23.6 | 19.2 |
| $C_{8-16}$ Alkyl glucoside | 28.1 | 31.2 | 25.4 |
| 1,2-Propylene glycol | 9.5 | — | 15.5 |
| Water | 34.0 | 39.7 | 32.2 |
| Appearance | Cloudy | Cloudy | Cloudy |
| Polariz. microscope | Lamellar | Lamellar | Lamellar |

The concentrates were prepared by mixing the lipids, the dispersant and the vitamins above the melting temperature of the lipid, in the present case at 60° C., and mixing with water and optionally propylene glycol (to reduce the viscosity of the lamellar gel phase).

1.2 Microemulsifiction

|  | M1 | M2 |
|---|---|---|
| Vitamin E acetate | 1.0 | 1.0 |
| Vitamin F (linoleic acid) | 2.0 | 2.0 |
| Cetyl palmitate | 30.0 | 30.0 |
| Hydrogenated castor oil | 2.5 | 2.5 |
| Glycerol monopalmitate | — | 0.7 |
| Behenyl alcohol + 10 EO | 10.0 | 9.3 |
| Water | 54.5 | 54.5 |
| Appearance | White-bluish | White-bluish |
| Particle size [nm] | 172* | 199* |

*as measured by laser light scattering (Malvern "Zetasizer")

The microemulsions were prepared by the so-called PIT (phase inversion temperature) process. The wax (cetyl palmitate), the hydrogenated castor oil, the emulsifiers (glycerol monopalmitate, behenyl alcohol ethoxylate) and the oil-soluble active substances are heated with the water to a temperature above the phase inversion temperature (in the present case to 80° C.), intensively mixed and cooled while stirring to normal temperature (20° C.). Shimmering blue very fine-droplet emulsions containing wax nanoparticles with a particle size below 200 nm are formed.

2. Vitamin-containing surfactant formulations

A shower bath formulation D1 with the following composition was used:

|  | D1 |
| --- | --- |
| Na lauryl sulfate (1) | 10.0% by weight |
| Cocofatty acid protein condensate (2) | 1.0% by weight |
| Cocoamidopropyl betaine (3) | 1.0% by weight |
| $C_{10-16}$ alkyl glucoside (4) | 4.0% by weight |
| Glycerol $(EO)_7$ fatty acid ester (5) | 1.0% by weight |
| $C_{12-14}$ fatty alcohol + 2 EO (6) | 0.5% by weight |
| Na benzoate | 0.4% by weight |
| p-hydroxybenzoic acid ester | 0.3% by weight |
| Na lactate | 0.2% by weight |
| Lactic acid | 0.6% by weight |
| d-Panthenol | 0.2% by weight |
| NaCl | 0.5% by weight |
| Water | to 100 |

The formulation was prepared by mixing the components at room temperature.

The percentages by weight shown above are based on 100% active substance. The commercial products used (Henkel KGaA) are as follows:

(1) Texapon® 70
(2) Lamepon® S
(3) Dehyton® K
(4) Plantaren® 1200 CSUP
(5) Cetiol® HE
(6) Arlypon® F The following vitamin-containing formulations were prepared from the mixtures:

|  | 1 | 2 | 3 | C |
| --- | --- | --- | --- | --- |
| Shower bath D1 | 94% | 92.5% | 95% | 99.7% |
| Concentrate M1 | 6% | — | — | — |
| Concentrate S1 | — | 7.5% | — | — |
| Concentrate S2 | — | — | 5% | — |
| Vitamin E acetate | — | — | — | 0.1% |
| Vitamin F (linoleic acid) | — | — | — | 0.2% |
| Appearance | Bluish white | Cloudy lamellar | Clear isotropic | Clear isotropic |
| Particle size [nm] | 172* | 1250** | — | — |

The formulations were prepared by mixing at room temperature. Comparison formulation C was prepared in the usual way similarly to shower bath D1, the active substances being solubilized in the surfactants.

Depending on the quantity of liquid crystal solubilizates incorporated, the products obtained were cloudy products (S1) containing lamellar microspheres or transparent mixed micelle solubilizates (S2).

Particle size was measured by laser light scattering (Malvem "Zetasizer") in the case of formulation 1 and by video microscopy and digital particle size determination (optimetries) in the case of formulation 2.

3. Penetration studies (vitamin E acetate)

For formulations 1 and 3 and comparison formulation C with conventionally incorporated active substances, penetration studies were performed on a perfused cow's udder (BUS Model—Bovine Udder Skin Model). This method is described in detail, for example, in ALTEX 12, 4/95, pages 196–200.

15 Minutes after the beginning of the perfusion, quantities of 4 g of the formulations were applied to 100 $cm^2$ areas of skin. After a contact time of 2 minutes, the cleaning formulation was thoroughly rinsed off with 2 liters of warm (40° C.) water using a sponge and the area of skin was dried with a paper towel.

This cleaning process was repeated three times in order to take into account possible accumulation effects. The upper layers of the Stratum corneum were then stripped off using Tesa® -Strip film (Tesa Type 4204, Beiersdorf). 10 Strippings were carried out which corresponds in all to an approximately 10 $\mu$m thick layer of the Stratum corneum. 1.10 mg of horny cells were removed per Tesa-Strip (1.9× $10^2$); standard deviation ±0.36 mg for n=20.

The vitamin E acetate was analytically determined in the skin samples. To this end, the Tesa strippings were extracted and the vitamin E acetate was isolated in the extract was isolated and substance-specifically determined by liquid chromatography. Quantification was achieved by standard calibration and comparison with blank samples (untreated areas of skin).

The following penetration results were obtained:

|  | 1 | 3 | C | Blank value |
| --- | --- | --- | --- | --- |
| Tesa-Strip 1–3 (cumulative) $\mu$g | 1.66 | 1.69 | 0.72 | <0.04 |
| Tesa-Strip 1–10 (cumulative) $\mu$g | 3.48 | 2.73 | 1.16 | <0.13 |

What is claimed is:

1. An aqueous body wash composition comprising:
   (a) at least 5 percent by weight of a water-soluble surfactant or surfactants; and
   (b) at least 0.05 percent by weight of a lipid-soluble, water-insoluble active substance, wherein the active substance is solubilized with a polar lipid in a lipid/surfactant mixed micelle or liquid crystal, or is microemulsified with a non-polar lipid wherein the emulsion droplets have a diameter of less than 500 nm, and wherein The water-soluble surfactant or surfactants comprise (i) a mixture of an anionic sulfate or sulfonate surfactant and a zwitterionic betaine surfactant, or (ii) a mixture of an anionic surface and an alkyl glycoside surfactant.

2. The aqueous body wash composition of claim 1 wherein the amount of the water soluble surfactant or surfactants is sufficient to solubilize or microemulsify said active substance to render said composition washable with water.

3. The aqueous body wash composition of claim 2 wherein the water soluble surfactant or surfactants is present in the composition in an amount from 5 to 30 percent by weight.

4. The aqueous body wash composition of claim 1 wherein the water-soluble surfactant comprises the mixture of the anionic sulfate or sulfonate surfactant and the zwitterionic betaine surfactant.

5. The aqueous body wash composition of claim 1 wherein the water-soluble surfactant comprises the mixture of the anionic surfactant and the alkyl glycoside surfactant.

6. The aqueous body wash composition of claim 1 comprising 0.1 to 1 percent by weight of the lipid-soluble active substance.

7. The aqueous body wash composition of claim 1 comprising a lipid-soluble vitamin as the active substance.

8. The aqueous body wash composition of claim 1 comprising tocopherols or lipid-soluble derivatives thereof as the active substance.

9. The aqueous body wash composition of claim 1 wherein the polar lipid comprises a linear $C_{12-22}$ fatty alcohol, a linear $C_{12-22}$ alkanediol, a $C_{12-22}$ fatty acid partial ester of a $C_{3-8}$ polyol containing 2 to 6 hydroxyl groups or a $C_{8-2}$ fatty acid monoalkanolamide of a $C_2$ or $C_3$ alkanolamine.

10. The aqueous body wash composition of claim 1 wherein the non-polar lipid comprises a paraffin solid at 20° C., a fatty acid ($C_{12-22}$) triglyceride, a wax ester or a mixture thereof.

11. The aqueous body wash composition of claim 1 wherein the weight ratio of the polar lipid or the non-polar lipid to the active substance is from 5:1 to 50:1.

12. The aqueous body wash composition of claim 1 wherein the emulsion droplets have a diameter of 100 to 200 nm.

13. A process of washing or cleansing skin or hair comprising forming an aqueous body wash composition according to claim 1, applying a washing or cleansing-effective amount of said aqueous body wash composition to the skin or hair for a time sufficient to effect washing or cleansing of the skin or hair, and removing said aqueous body wash composition with water, whereby the active substance is absorbed into the skin or hair.

14. The process of claim 13 wherein the aqueous body wash composition is formed by first forming a concentrate comprising 1 to 10 percent by weight of the active substance solubilized in lipid/surfactant mixed micelle or liquid crystal, then mixing said concentrate with an aqueous body wash.

15. The process of claim 14 wherein the weight ratio of the lipid to the surfactant is 1:2 to 2:1 and the weight ratio of the polar lipid to the active substance is 10:0.2 to 10:2.

* * * * *

UNITED STATES PATENT AND TRADEMARK OFFICE
CERTIFICATE OF CORRECTION

PATENT NO.    : 6,303,109 B1
DATED         : October 16, 2001
INVENTOR(S)   : Foerster et al.

It is certified that error appears in the above-identified patent and that said Letters Patent is hereby corrected as shown below:

Column 6,
Line 33, delete "The", and insert therefor -- the --.
Line 36, delete "surface", and insert therefor -- surfactant --.
Line 66, delete "$C_{8-2}$", and insert therefor -- $C_{8-22}$ --.

Column 8,
Line 7, after "solubilized in", insert -- a --.

Signed and Sealed this

Twenty-sixth Day of August, 2003

JAMES E. ROGAN
*Director of the United States Patent and Trademark Office*